United States Patent [19]
Dumais et al.

[11] Patent Number: 5,641,626
[45] Date of Patent: Jun. 24, 1997

[54] HIGHLY DERIVATIZED AGAROSE CONFORMATIONAL NUCLEIC ACID SEPARATION

[75] Inventors: Maxine Dumais, Union; Noriko Kusukawa; Hugh White, both of Camden, all of Me.

[73] Assignee: FMC Corporation, Philadelphia, Pa.

[21] Appl. No.: 146,286

[22] Filed: Oct. 29, 1993

[51] Int. Cl.$^6$ .......................... C12Q 1/68; H01L 29/788
[52] U.S. Cl. ........................ 435/6; 436/94; 252/315.3
[58] Field of Search ................. 435/6; 252/315.3; 436/94

[56] References Cited

U.S. PATENT DOCUMENTS

| | | | |
|---|---|---|---|
| 3,956,273 | 5/1976 | Guiseley | 260/209 |
| 4,275,196 | 6/1981 | Shainoff | 536/115 |
| 4,319,975 | 3/1982 | Cook | 204/180 |
| 4,504,641 | 3/1985 | Nochumson | 526/238.2 |
| 5,143,646 | 9/1992 | Nochumson et al. | 252/315.3 |
| 5,212,299 | 5/1993 | Smith | 536/114 |

OTHER PUBLICATIONS

Nochumson et al., *Electrophoresis*, 81:213–218 (1981).
Guiseley, Industrial Polysaccharides, ed. M. Yalpani, Elsevier, 1987.
FMC BioProducts Group Technical Bulletin p–18.
Stellwagen, *BioChemistry*, 22:6186–6193 (1983).
Stellwagen, *Biopolymers*, 30:309–324 (1990).
Serwer, *Electrophoresis* 4:375–382 (1993).
Lane et al., Microbiological Review, pp. 509–528 (1992).
Lilley, et al., Biochem. Soc. Trans. 21:111–116 (1993).
Hjerten, et al. *Biomedical Chromatography*, 8:73–76 (1994).
Griess, et al. *Journal of Structural Biology*, 111:39–47 (1993).
FMC BioProducts 1993 Catalogue, p. 55.
Bolshoy, A. et al. Curved DNA Without A–A: Experimental Estimation of all 16 DNA Wedge Angles. Proc Natl. Acad Sci. USA (Mar. 1991) 88:2312–2316.

*Primary Examiner*—Kenneth R. Horlick
*Attorney, Agent, or Firm*—Polly E. Ramstad; Mark A. Greenfield; Robert L. Andersen

[57] ABSTRACT

Compositions for the gel electrophoresis separation of conformational isomers of nucleic acids and agarose compositions useful in such compositions. The compositions use compositions comprising: at least one aqueous gel which is at least one highly derivatized agarose derivatized sufficiently to reduce its gelling temperature (Tg) to below 17° C., present in 40 wt % or more based upon the gel total weight, in admixture with at least one high gel-strength polysaccharide aqueous gel other than polyacrylamide in a balance to 100% total gel weight; and an electrophoretic buffer, present in an electrophoretic buffer—effective amount. The invention compositions comprise at least one aqueous gel comprising at least one agarose derivatized sufficiently to reduce its gelling temperature (Tg) to below 9° C., present in 40 wt % or more based upon the gel total weight, in admixture with at least one high strength non-acrylamide polysaccharide present in a balance to 100% total gel weight; and an electrophoretic buffer, present in an electrophoretic buffer—effective amount.

33 Claims, 5 Drawing Sheets

HIGHLY DERIVATIZED AGAROSE CONFORMATIONAL NUCLEIC ACID SEPARATION

BACKGROUND OF THE INVENTION

1. Field of the Invention

This invention is directed to methods for the gel electrophoresis separation of conformational isomers of nucleic acids, and to agarose compositions useful in such methods. The methods are distinguished by their ability to separate DNA by conformation as well as by molecular weight.

2. Description of the Related Art

It is well known to separate molecules according to their molecular weight by gel electrophoresis. The gels most commonly used for such purposes comprise agarose (a natural polysaccharide polymer) and cross-linked polyacrylamide. Traditionally, agarose gels have been used for the separation of larger molecules, such as double-stranded DNA with molecular sizes over 500 base pair (bp), while polyacrylamide gels (PAG) have been preferred for smaller molecules. Agaroses which are more sieving have become available. Nochumson, et al., *Electrophoresis* 81:213–218, (1981) showed that very-low melting temperature agarose such as "SeaPrep" agarose (a product of FMC Corporation, BioProducts Group, Philadelphia, Pa., U.S.A.) could be used for electrophoresis. Methods for making such agaroses are disclosed in U.S. Pat. No. 3,956,273—Guiseley, and reviewed by Guiseley in *Industrial Polysaccharides*, ed. M Yalpani, Elsevier, 1987; p. 139–147. In the latter publication, Guiseley shows that there is a linear relationship between the degree of substitution of an agarose and the reduction in gelling temperature (Tg) obtained by substitution. U.S. Pat. No. 4,319,975—Cook discloses that derivatized agarose gels have improved sieving capability compared to underivatized agarose of the same concentration. Other derivatized agaroses are described by Smith (U.S. Pat. No. 5,212,299), Shainoff (U.S. Pat. No. 4,275,196), and Nochumson (U.S. Pat. No. 4,504,641). U.S. Pat. No. 5,143,646—Nochumson, et al., discloses especially effective combinations of derivatized agarose (for sieving power) and partially depolymerized agarose (to control viscosity). An example of an agarose composition according to U.S. Pat. No. 5,143,646 is sold under the trademark "MetaPhor" by FMC Corporation, BioProducts Group, Philadelphia, Pa., U.S.A. This composition is useful as a gel for non-conformational electrophoretic separations and may comprise two hydrogels, at least one of which has been derivatized and independently at least one of which has been depolymerized sufficiently to reduce the casting-effective viscosity of the total gel composition, together with a resolving gel buffer. U.S. Pat. No. 5,143,646 further discloses that the degree of derivatization and to a lesser extent the concentration of the hydrocolloid (agarose) may be such that the gelling temperatures (Tg) are 10° C.–25° C., and further states that a Tg below about 10° C. gives rise to weak or fragile gels which tend to crack whereas a Tg above 25° C. falls off in sieving capacity (col 6). As described in FMC Corporation BioProducts Group technical bulletin P-18, MetaPhor agarose compositions can reliably separate DNA fragments differing in size by about 2%, or 4 base pairs, at 200 base pairs and higher, in non-denaturing systems. However, this degree of resolution is still not as discriminating as acrylamide gels can be. Stellwagen in *Biochemistry* 22:6186–6193, (1983) showed that in acrylamide gels, but not in agarose gels (p. 6186), fragments of DNA can migrate differently depending on their intrinsic conformation. In further work, Stellwagen in *Biopolymers* 30:309–324, (1990) indicated that the migration of a pair of DNA fragments, both having 147 base pairs, shows this effect clearly in standard polyacrylamide gels. The article states that " . . . pore size alone is not responsible for the anomalous electrophoretic mobilities . . . in polyacrylamide gels . . . " (p.323, last paragraph), and further states that the two fragments differed in their particular conformation, with one of the conformational isomers being "bent", and therefore retarded in its migration. Why the effect occurred in polyacrylamide but not agarose remains unclear.

DISCUSSION OF CONFORMATIONAL ISOMER SEPARATION

The anomalous mobilities of conformational separation need to be distinguished from conventional separations by molecular weight. In molecular weight-based separations molecules of differing molecular weight are differentially retarded in proportion to their molecular weight by the sieving action of the gel strands. The properties of a given gel can be determined by various mathematically derived quantities, such as "Kr" [see Serwer, *Electrophoresis* 4:375–382, (1983)], which describe the relative separation, after gel electrophoresis, of molecules sharing common chemical and conformational properties. Examples of such well-behaved classes of molecules include most DNA molecules, and sodium dodecyl sulfate-protein complexes. Separation by conformation anomalies is then superimposed on a background of separation by molecular weight. A distinguishing feature of a conformational-based separation is that the differences between conformational isomers of molecules are greater than would be expected solely on the basis of molecular weight. For example, the two 147 bp fragments discussed above have a net molecular weight difference of about 200 daltons (see FIG. 1), which is less than ⅓ of the weight of one base pair, or less than 0.2% of the weight of the fragments. This is substantially less than the size differences separatable on highly specialized agarose gels, (such as sequencing gels), which are designed to separate DNA molecules by weight when the differential is only one base. In the case of the 147 bp fragments, the separation between the bands is clearly visible on acrylamide gels, and on agarose gel compositions having the properties of the subject invention. This separation corresponds to a difference of 2 or more base pairs on a prior art agarose gel which otherwise has the same sieving power. Similarity in sieving power is determined by equivalence in migration of molecules which are not conformationally anomalous; most common molecular weight marker sets are selected to consist of such molecules. The term "conformational isomers" is used here in a restricted sense. There are some classes of nucleic acids, especially of DNA, which are commonly referred to in the literature as "topological isomers" but which also have conformational differences. In particular, the differences among linear DNA, closed-circular ("relaxed") DNA, and supercoiled DNA (all of which are topological isomers) give sufficiently large conformational differences to be separated readily on conventional agarose gels. The conformational isomers which are separable by the agarose gels of the invention are restricted to those involving linear nucleic acids. Moreover, the nucleic acids of interest are typically smaller fragments, with less than about 2000 bases (single stranded) or base pairs (double stranded), and more typically with 500 or fewer bases or base pairs.

There are a variety of types of electrophoretic conformational separations (assays) in current use. The 147 bp isomers discussed above are one of the most demanding of these separations. Another type of conformational separation is Single Strand Conformational Polymorphism (SSCP) analysis, often used to distinguish single-base pair or larger changes in DNA and RNA molecules. A further type is a "heteroduplex/homoduplex" assay in which a perfect match of two complementary nucleic acid strands (homoduplex) is distinguished from a match in which one or more base pairs are mismatched (heteroduplex). Examples of these two types of separation assays are found in Examples 25 and 26. An additional conformational separation possible with the present invention is a method for the detection of specific DNA-protein interactions by using a "gel shift" assay which involves the separation of DNA-protein complexes wherein the mobility of the DNA in the complex is altered from its mobility in the free state due to the presence of bound protein and changes (bends) to its conformation [see Lane, et al., in *Microbiological Review* p.509–528 (1992)]. There are many other variants of conformational separations. Lilley, et al., [*Biochem. Soc. Trans.* 21:111–116, (1993)] reviewed a variety of types of conformationally-based separations of nucleic acids (DNA and RNA), such as "bubbles", and noted (p. 111) that others had found that " . . . they had to include the elastic properties of the [acrylamide] gel matrix to obtain a good fit . . . ". Other conformational separations of this type are also included in the definition of conformational separations.

SUMMARY OF THE INVENTION

This invention comprises electrophoretic methods for the separation of conformational isomerisms by the anomalous migration of DNA or RNA nucleotide fragments using a specific range of compositions, and a narrower range of the compositions themselves, all containing as a critical ingredient highly derivatized agaroses with a specific degree of substitution as measured by their gelling temperatures. The compositions, to be effective in this invention, must have sufficient gel strength and low enough viscosity to permit casting and handling. The inventive mechanism is distinguishable from conventional agarose gel sieving, in that while prior art agarose compositions have comparable or greater sieving power, and comparably narrow band sharpness (resolution), they cannot separate conformational isomers. This invention further comprises methods for the detection of point mutations using separation assays based on SSCP, heteroduplex, and gel shift analysis.

BRIEF DESCRIPTION OF THE DRAWING

FIGS. 2A and 2B were both vertical 16×26×0.1 cm gels run in C.B.S. Dual Adjustable Slab Gel Unit Model #DAS6-250 under running conditions of 19.2 V/cm for 1.5 hours. Both FIGS. 2A and 2B have five lanes numbered at the top wherein: Lane 1 is 0.4 micrograms pBR322/MspI; Lane 2 is 0.6 micrograms 100 bp ladder; Lane 3 is a mixture of 100 bp ladder and pBR322/MspI, 0.6 micrograms and 0.4 micrograms DNA respectively; Lane 4 is a mixture of 100 bp ladder and 1 kbp ladder, 0.6 micrograms for both; and Lane 5 is 0.6 micrograms 1 kbp ladder. FIG. 2A was run on 4% inventive highly derivatized agarose/high gel-strength agarose gel with TBE buffer (1×), and FIG. 2B was run on 4% MetaPhor (prior art) gel with TBE buffer (1×). A 17 to 30 cm scale is shown on the right and the 147 bp point is shown on the left. Additional information related to this figure is given in Example 22.

FIGS. 3A and 3B were gels both run on the Hoefer SE 600 series vertical slab gel unit. The gel dimensions were 18×16×0.1 cm. The gels were electrophoresed at 31 V/cm for 1 hour in 0.5×TDE running buffer. The DNA was from Stratagene's SSCP-PCR+ Control Kit. Both FIG. 3A and FIG. 3B use three lanes, identified from right to left as: MD (Mutant Denatured); CD (Wild-Type Denatured); and C (Non-Denatured Wild-Type). Both Figures identify the points of 250 bp double stranded DNA and single strand DNA. Additional information relating to this figure is found in Example 25.

FIGS. 4A and 4B were gels both run on the C.B.S. Dual Adjustable Slab Gel Unit Model #DAS6-250 at 19 V/cm for 2 hours using 1×TBE running buffer. The heteroduplex control was DNA from AT Biochem. FIG. 4A used an inventive gel at 4% while FIG. 4B used the prior art MetaPhor gel at 4%. Identified points are the heteroduplex and the 350 bp homoduplex. Additional information relating to this figure is found in Example 24.

DETAILED DESCRIPTION OF THE INVENTION

Figure 1:
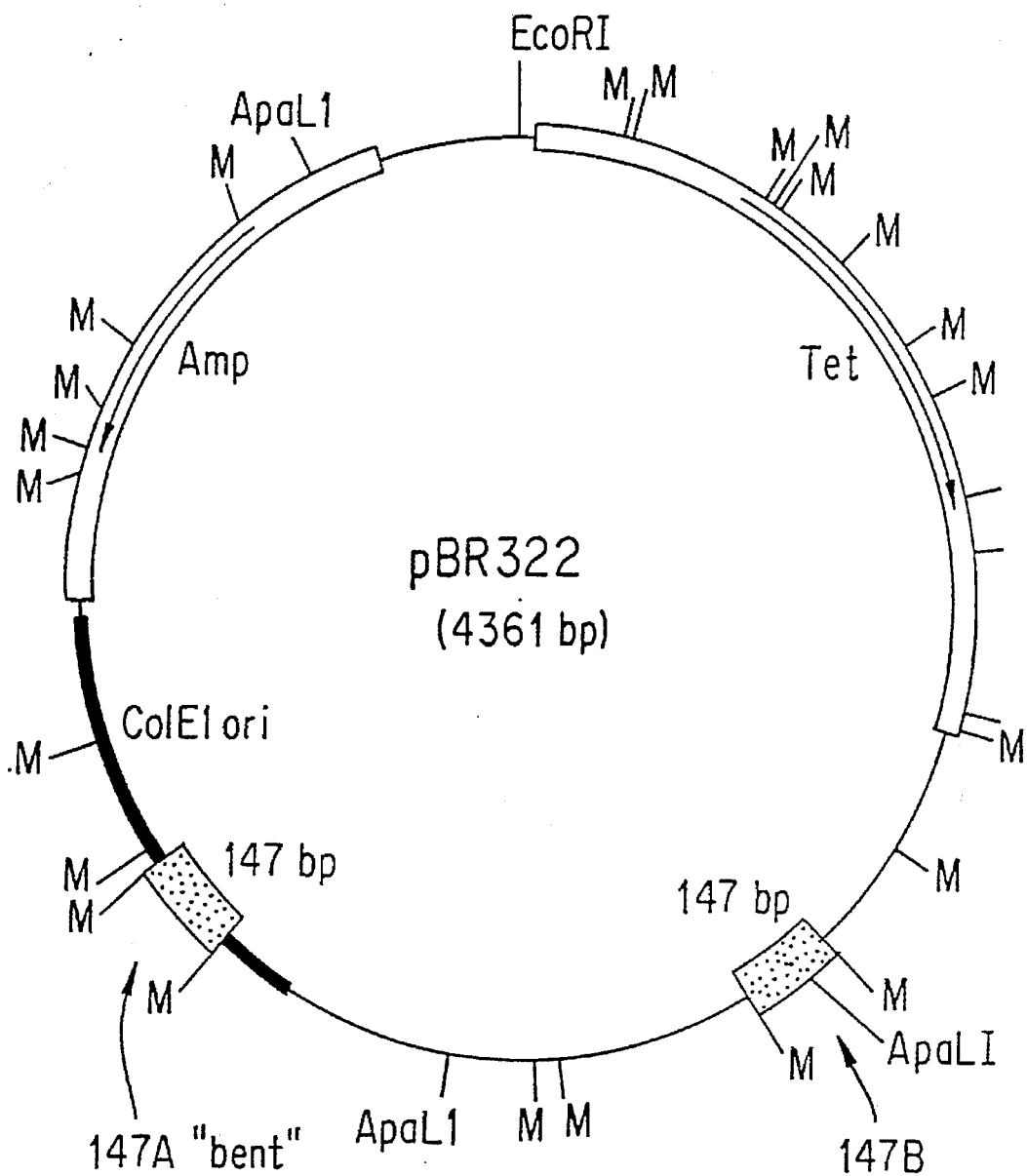
FIG. 1 shows a map of pBR322 under restriction with the enzyme Msp I. The two 147 bp fragments, one anomalous, are located, according to Stellwagon & Stellwagon 1990 *Biopolymers* 30:309–324.

Other than in the operating examples, or where otherwise indicated, all numbers expressing quantities of ingredients, parameters, or reaction conditions used herein are to be understood as modified in all instances by the term "about".

I. A first series of embodiments of this invention are methods for the electrophoretic separation of conformational nucleic acid isomers using compositions comprising:

A) at least one aqueous gel which is
  (1) at least one highly derivatized agarose derivatized sufficiently to reduce its gelling temperature (Tg)—as measured at 0.8 wt % concentration—to below 17° C., present in 40 wt % or more based upon the gel total weight, in admixture with
  (2) at least one high gel-strength hydrocolloid matrix gel other than polyacrylamide in a balance to 100% total gel weight; and preferably B) an electrophoretic buffer, present in an electrophoretic buffer—effective amount.

In these method embodiments other aspects of conducting the conformation-based separations of this invention are in accordance with electrophoretic separations known in the art in connection with conventional weight-based separations.

II. A second series of embodiments of this invention are novel compositions for the electrophoretic separation of conformational nucleic acid isomers comprising:

A) at least one aqueous gel comprising
  (1) at least one agarose derivatized sufficiently to reduce its gelling temperature (Tg)—as measured at 0.8 wt % concentration—to below 9° C., present in 40 wt % or more based upon the gel total weight, in admixture with
  (2) at least one high strength non-acrylamide hydrocolloid matrix gel present in a balance to 100% total gel weight; and B) an electrophoretic buffer, present in an electrophoretic buffer—effective amount.

III. A third embodiment of this invention, spanning both Embodiments I and II, is that the inventive methods and compositions can be used for the detection of point mutations by single strand conformational polymorphism (SSCP), heteroduplex/homoduplex, or gel shift analyses.

This embodiment can be used for diagnostic tests or general research methods. In particular, this embodiment may permit assays in standard horizontal gels, rather than the more difficult vertical gels.

In all of the above embodiments, the highly derivatized agarose is substituted with a: $C_{1-4}$ alkyl; hydroxy, dihydroxy or polyhydroxy-($C_{1-5}$) alkyl; an ester or ether of the foregoing with a $Cl_{1-4}$ neutral moiety having 0 or 1 to 3 oxygen atoms; or is a mixture of these derivatized agaroses. A preferred highly derivatized agarose is hydroxyethyl agarose. The critical distinction between the highly derivatized agaroses of this invention and those known in the art is the narrow useful range of their degree of substitution as measured by their gelling temperature. Most specifically, the term "highly derivatized" refers only to those derivatized agaroses whose Tg ranges are limited to those disclosed elsewhere in this specification as defining the compositions useful in the inventive methods or inventive compositions themselves. The manner of derivatization of the agaroses is known in the art disclosed in the related art discussion in this specification and does not form a part of the invention.

The starting material for the preparation of the at least one highly derivatized agarose can be any of a variety of agaroses, including any native agarose from the usual commercial genera (including, but not limited to, Gracilaria, Gelidium, and Pterocladia), viscosity-reduced partially depolymerized native agaroses (preferably with viscosities in the range of about 20 to 60 milliPascals (mPa), at 3% and 70° C.), and even agaroses which are partially (but not sufficiently) derivatized. The degree of derivatization will be reflected directly in the gelling temperature (Tg). The derivatizing agents needed to produce the target Tg are known in the art and the amount of agent required will vary with the starting seaweed species, being increased according to the degree of natural methylation possessed by the agarose. The derivatization of the at least one agarose according to this invention is itself known in the art.

A critical distinction must be made between the degree of substitution [as measured by the gelling temperature (Tg)] of the at least one highly derivatized agarose of the first and second series of embodiments of this invention. Agarose with a Tg of 10° C. or above is itself known in the art (see previously discussed U.S. Pat. No. 5,143,646 at col. 6), and agaroses with a Tg of 9° C. or more are believed to have been sold. Therefore the novel compositions of this invention are limited to those containing highly derivatized agaroses with a Tg of less than 9° C. However, the use of the inventive compositions for the conformational separation methods of this invention is not known in the art and for the compositions used in the inventive methods according to this invention, the Tg may be up to less than 17° C.

The amount of the highly derivatized agarose present in the method and composition embodiments of this invention may be (in order of preferability): from 40 wt % up to 100 wt %; from 40 wt % up to less than 100 wt %; 60 wt % up to less than 100 wt %; 60 wt % up to 90 wt %; and 70 wt % up to 90 wt %. An amount of 80 wt % has been used in many of the examples herein for the sake of uniformity of comparison and approximately 80 wt % may be considered particularly useful when the highly derivatized agarose is a hydroxyethyl agarose within the Tg ranges disclosed as preferable. All of these weight percentages are based upon the total weight of the gel composition.

The high gel-strength hydrocolloid matrix gel may itself be one or a blend of materials. The functional reason for using the inventive gel compositions rather than single gels is to facilitate handling during electrophoretic procedures by increasing gel strength and/or general mechanical strength, and adjusting the gel's viscosity, when needed.

Useful high strength gels include: one or more agaroses (such as LE, Gold, or HSB—as elsewhere defined herein); lower molecular weight agaroses, (such as LE irradiated with up to 600 kR of gamma irradiation, or HSB reduced to a viscosity of 25 to 55 mPa's at 70° C. and a concentration of 3.0%; hydroxyethylated or derivatized native or viscosity-reduced agaroses); and neutral (non-ionic) gelling polymers such as curdlan, konjac, beta-carrageenan, and their blends and chemical derivatives. Preferred high strength gels are: agaroses such as LE, Gold, or HSB; lower molecular weight agaroses such as LE irradiated with up to 600 kR of gamma irradiation or HSB reduced to a viscosity of 25 to 55 mPa's at 70° C. and a concentration of 3.0%; and neutral (non-ionic) gelling polymers are contemplated, such as curdlan, konjac, beta-carrageenan, gelatin, chitin and their blends and chemical derivatives. The most preferred hydrocolloid matrices comprise high gel strength agaroses, such as LE, Gold, or HSB.

The high gel-strength hydrocolloid gels (the second gel component of the inventive compositions) when present, function as matrices which permit the highly derivatized agarose gel component to function as the electrophoretic medium. As is known in the electrophoresis art, it is necessary for electrophoretic gels to be cast prior to use, after which it may be necessary to handle them in various manners in order to conduct elctrophoresis separation. For this reason the high gel-strength hydrocolloid, (which preferably is in all of the inventive compositions), is present minimally in a matrix-effective amount. It should be apparent that the two components of the gel composition must be compatible with each other in forming a single composite gel, and cannot be biphasic. Where the second gel component is itself an agarose, it must: [1] be handlable for electrophoresis purposes, [2] maintain its structural integrity, and [3] afford minimal swelling. In particular, when the second component is an agarose, it should have a gel strength of at least 500 g/cm at 1% w/w concentration.

The total concentration (in water) of agaroses and other gel-forming materials in the final gel will vary depending on the size of the molecules in which the conformational differences are to be observed or separated. The appropriate concentration for optimizing the separation can be selected, using criteria known in the art. Minimum effective total concentrations are about 2% to have sufficient mechanical strength, with 3% being more effective and 4 to 6% most preferred. Upper concentration limits for effective conformational separations have not been observed. However, as the gel concentration becomes higher, the viscosity of the gel-forming solutions increases, making handling more difficult. Moreover, the sieving power, or retarding power, of the gel increases, eventually requiring unduly long running times to obtain the desired separation. Thus, concentrations above about 15% are generally impractical due to viscosity; concentrations above 10% are likely to be too sieving; and concentrations below 8% are preferred, with the aforesaid 4 to 6% concentration being most preferred.

In addition to the gelling polymers and water, the inventive compositions include a buffer. The exact buffer is not a critical aspect of the invention. Any buffer known or believed in the art to support the separation is suitable. Buffers commonly used in other types of electrophoresis separation, such as TAE or TBE, are useful. TAE is Tris-Acetate-EDTA, respectively 40,40, and 1 mM at 1×strength, pH about 8.6; TBE is Tris-Borate-EDTA, concentration (1×strength) 89,89, and 1 mM, pH about 8.6. While it is known that electrophoresis separations can be made in the absence of buffer, as in isoelectric focussing, this is not preferred.

Also contemplated, but not of essence in the invention, are optional additives to preserve gels against drying, improve optical properties, or otherwise to assist in the process of making, using, and handling gels. These are known in the art, and include humectants such as glycerol, glycols, and other low molecular weight polyhydroxy compounds including inositol and the like, and sugars; polymeric additives to control syneresis or to adjust mobility characteristics, such as linear polyacrylamide, locust bean gum, polyvinyl alcohol, polyethylene glycol, hydroxyethylcellulose, and the like. Also contemplated are dyes, such as ethidium bromide, and other additives as known in the art. The total weight of additives, as a percent of the weight of the final gel composition, may be as high as 20%, and is more typically in the range of 5 to 10%; the exact amount and nature of such additives is not a part of the invention.

Definitions Used Herein:

In describing agaroses herein, LE refers to "SeaKem" LE agarose, an underivatized agarose; SPQ refers to "SeaPlaque" hydroxyethyl-derivatized agarose; SPR refers to "SeaPrep" hydroxyethyl-derivatized agarose; Gold refers to "SeaKem Gold" underivatized agarose; and "AcrylAide" refers to agarose derivatized with allylglycidyl ether. The preceding are prepared from Gelidium species. HSB refers to an underivatized agarose prepared from Gracilaria species. SeaKem, SeaPlaque, SeaPrep, SeaKem Gold, and AcrylAide are all trademarks of FMC Corporation, BioProducts Group, Philadelphia, Pa., U.S.A.

Prior art gels made of crosslinked polyacrylamide are referred to as "acrylamide" gels or as "PAG". When a linear non-crosslinked polyacrylamide or acrylamide monomer is intended, it is so described.

"Derivatized" as used herein means treated with a chemical reagent which results in the addition of moieties to the polymer. The term "modified", as used in U.S. Pat. No. 3,956,273—Guiseley, is the equivalent. The term "substituted", in the sense of chemical substitution, also is equivalent. The term "degree of substitution" refers to the average number of added moieties per agarobiose (disaccharide) unit. The maximum theoretical number is four.

"Tg" is used herein to designate the gelling temperature (not glass transition temperature) of a gel, measured as described below. It should be noted that the Tg of a given gel corresponds directly to its degree of substitution (D.S.) and is commonly used today instead of the D.S. All temperatures are in degrees celsius.

Compositions of this invention:

Methods: The gelling temperature (Tg) of these gels is measured by the "Sand Test". Tg is significantly affected by the gel concentration, especially in the compositions of interest in this invention. Moreover, the measured values will depend on how the test is conducted.

Gelling temperature (Tg): A 0.8% gel is made by dissolving 0.128 grams of agarose in 16 g distilled water in a test tube. The agarose is brought to a boil by placing the test tube in a boiling water bath or over a Bunsen burner. The slurry is heated long enough to ensure complete dissolution. The solution is then placed in a room temperature water bath and the temperature is slowly decreased at the rate of 0.5° C. per minute by adding ice. For each 0.5° C. drop, a few grains of Ottawa Sand are added. When the sand no longer drops through the solution, but remains stationary, the temperature is recorded as the gelling temperature.

Gel strength is the force required to rupture a gel, in grams/square centimeter as described. It is measured as follows: Four grams of agarose are dispersed into 200 mL distilled water (2% solution). The slurry is brought to a boil and boiled for five minutes. The solution is removed from the heating plate and brought back to weight with distilled water. The solution is then cooled to about 70° C. and poured into a crystallizing dish, filling to overflow. The dish is covered with a flat glass plate and placed in a refrigerated waterbath for two hours. The gel is then inverted in the dish which is then placed on a dietary balance pan. An MCD gel tester, available from FMC, has a 1 square centimeter plunger which descends at a fixed rate, depressing the gel surface. When sufficient force is applied to rupture the gel the indicator pointer snaps back. The maximum deflection is recorded as the breaking force. An average of three break-force readings are recorded as the break force for the gel.

Viscosity is measured at 3.0 wt % aqueous solution, 70° C., using a Brookfield LVT viscometer with a UL Adapter. The 3% aqueous solution of agarose is prepared in a tared 100 mL beaker by adding 1.5 g to 50 mL distilled water. The agarose then is dissolved by heating in a microwave oven with intermittent mechanical agitation. Once the agarose is completely dissolved, the solution is brought back up to weight with distilled water, and then 16 mL are aliquotted into the UL Adapter. This is then placed into a 70° C. waterbath for the viscosity reading. Units are in mPa·s.

Gel preparation: Gels are all prepared in a similar manner. The agarose is dissolved in the buffer of choice, TAE or TBE, at the desired strength. The gel concentration desired will vary with the amount of agarose dissolved. The correct amount of agarose is weighed, then sprinkled into the the choice buffer with stirring. Once dispersed the agarose slurry is dissolved by heating in the microwave. The solution is then brought up to weight with distilled water and cast. The cast gel is allowed to sit on the bench at room temperature (about 22° C.) for 15 minutes, then cooled in a refrigerator for 30 minutes. It is then ready for use. Horizontal gels are run at 5 to 20 volts per cm. Vertical gels are run at 18 to 30 volts per cm. The gels used in screening for the 147 bp separation are normally vertical gels 18 cm (W)×16 cm (L)×1 mm (T). They are run in a Hoefer SE 600 electrophoresis chamber (Hoefer Scientific Instruments, San Francisco, Calif. U.S.A) at 30 V/cm for 1.5 Hr. The gel is made up in 0.5× TBE and run in 0.5× TBE. After electrophoresis the gels are stained in 1 microgram per milliliter ethidium bromide for 10 minutes. The gels are then photographed on a UV light box.

DNA samples: The pBR 322/Msp I digest was purchased from New England BioLabs Inc., Beverly, Mass., U.S.A. The DNA is made up to the desired concentration, normally 0.4 micrograms per 5 microliters. The loading dye is 30% Ficoll, 0.1M NaEDTA, 0.1% bromophenol blue comprising 10% of the total loading volume.

Molecular weight markers (100 bp ladder and 1 Kbp ladder) were purchased from Gibco BRL Life Technologies, Inc., Gaithersburg, Md. U.S.A. The mixtures of pBR322/Msp I and 100 bp ladder and 1 Kbp and 100 bp ladder were prepared in the lab by mixing the two markers together at the appropriate ratios.

Invention Single-Strand Conformational Polymorphism analysis was demonstrated using SSCP-PCR+ Control Kit DNA (from Stratagene, La Jolla, Calif., U.S.A). The kit consists of two plasmid DNA templates, one wild-type and one mutant-type, 250 bp in length. Each DNA fragment should resolve into three discrete bands. The two lighter intensity bands are the single-stranded strands, and the remaining higher intensity band is the nondenatured double-stranded DNA. A positive test is a difference in migration between the wild type and the mutant DNA single strands, either one or both strands migrating differently.

Invention Heteroduplex analysis was demonstrated using control DNA supplied in a Mutation Detection Enhancement Gel (MDE) kit (from AT Biochem, Inc., Malvern, Pa., U.S.A). The heteroduplex control DNA contains a 350 bp homoduplex DNA and single base mismatched heteroduplex DNA. A positive test shows the heteroduplex migrating slower than the homoduplex. The heteroduplex with ethidium staining shows up at about 25% the intensity of the homoduplex.

Invention 147 bp test: The determinative test criterion used for performance as a gel according to this invention was the ability to separate the two 147 bp fragments produced by digestion of the well-known plasmid pBR322 with the widely-available restriction endonuclease Msp I. When separated by (conformational) electrophoresis on a gel of an effective composition, the two 147 bp bands, 147A and 147B, are seen as a doublet with space between the bands. (Multiple other bands are present from the digestion, but run with different velocities in the gel.) The preparation and properties of the 147 bp DNA fragments are described in more detail in Stellwagen (1990), cited in the Description of Relevant Art.

Gels totally ineffective and therefore excluded from the present invention compositions and methods show the 147 bands with the same apparent thickness (along the electrophoresis migration direction) as bands known to be single-component. Gels of marginal use in the present invention show a broadening or blurring of the 147 band, but do not show clear separation of the band doublet. Such compositions may be of use in other inventive conformational separations, such as SSCP (single strand conformational polymorphism), but are not preferred. Confirmation that the separation of the 147 bp bands is not an artifact can be made by redigesting the Msp I digest of pBR322 with the enzyme ApaL I, which cleaves one of the pair of bands but not the other.

Compositions of the type most suitable for the practice of the methods according to this invention previously have not been of great practical interest because of their mechanical weakness (see U.S. Pat. No. 5,143,646 at col 6). For purposes of the invention the most critical aspect of the agarose component in the compositions used is that they have been highly derivatized, as that term is specified below. For compositions useful in the inventive methods the term "highly derivatized agarose" means that this component of such compositions has been derivatized to the extent that it has become non-gelling or has a maximum Tg range of: from the lowest temperature at which gellation will occur to 17° C.; preferably 0° C. to less than 9° C. or less than 17° C.; more preferably 2° C. to less than 17° C.; and most preferably 6° C. to less than 9° C.; 6° C. to 8° C. being particularly preferable.

Thus, the critical material components of the invention are particular classes of highly-derivatized low-melting agaroses, not previously thought to be useful. These materials, preferably in combination with reinforcing materials, preferably with a buffer, and optionally with conventional additives, allow the performance of a class of separations previously thought impossible on agarose gels.

EXAMPLES

Examples of materials and gel compositions of this invention and comparisons with non-inventive (and/or prior art) materials are given in Table 1. Explanations of abbreviations follow the table.

TABLE OF EXAMPLES

| COL: 1 EXAMPLE | 2 TYPE | 3 Tg @ 0.8% | 4 Amt Deriv | 5 GS 2% | 6 Fcn @ 4% | 7 Fcn OTHER % |
|---|---|---|---|---|---|---|
| 1 | LE | 34.0 | none | | NO | |
| 2 | SPQ | 27.5 | 0.35 lb/kg | 643 | NO | NO @ 6% |
| 3 | SPR | 16.5 | 1.3 lb/kg | 220 | NO | YES @ 100/6% |
| 4 | INVENTION | 14.5 | | | YES (90:10) | |
| 5 | INVENTION | 11.0 | | | YES (90:10) | |
| 6 | INVENTION | 10.0 | | | YES (90:10) | |
| 7 | INVENTION | 9.0 | | | YES (90:10) | |
| 8 | INVENTION | 8.0 | 29.2 ml/30 g | 140 | YES | |
| 9a | INVENTION | 7.0 | 2 lb/kg | 60 | YES | YES @ 60:40/4% |
| 9b | | | | | YES @ 100/5% | |
| 9c | | | | | BROAD @ 50:50/4% | |
| 10 | INVENTION | 2.0 | | 75 | YES | |
| 11 | INVENTION-V | 7.0 | 29.2 ml/30 g | 60 | YES | |
| 12 | HSB-VH | 39.5 | — | — | | — |
| 13 | MetaPhor | 20.0 | 16 ml/30 g | 173 | NO | NO @ 6% |
| 14 | INVENTION-VH | 15.5 | 24.1 ml/30 g | 135 | BROAD | |
| 15 | INVENTION-VH | 14.0 | 27.3 ml/30 g | 120 | BROAD | |
| 16 | INVENTION-VH | 7.5 | 32.5 ml/30 g | 72 | YES | |
| 17 | HE-HSB | 19.0 | 16.0 ml/30 g | 237 | NO | |
| 18 | HE-HSB | 18.0 | 24.1 ml/30 g | 162 | NO | |
| 19 | INVENTION-H | 7.5 | 32.5 ml/30 g | 88 | YES | |
| 20 | INVENTION (ex. 9 + LE) | | | | YES | |
| 21 | INVENTION (ex 9 + LE-V) | | | | YES | |
| 22 | INVENTION (ex 9 + HSB) | | | | YES | |
| 23 | INVENTION (AcrylAide <1) | | | | BROAD | |

Explanation of abbreviations:
 Col. 1: Example Number
  Column 2, Type: INVENTION, LE, HSB, SPQ, SPR, MetaPhor, AcrylAide are defined or described above. The suffix "V" indicates that the viscosity of the starting material was reduced by irradiation or other procedures. The suffix "H" means derived from Gracilaria (a "naturally methylated") agarose. The prefix "HE" means "hydroxyethylated".
 Col. 3, Tg at 0.8%: measurement performed as described in above methods on pure (not reinforced by matrix) highly derivatized agarose component.
 Col. 4, Amount of derivatizing reagent used: ethylene oxide, measured in pounds (as commercially supplied) of EtO per kilogram of starting agarose—one pound (lb) equals 0.45 kilograms; beta-chloroethanol, measured in mL/30 g of starting agarose. All derivatizing reactions were performed in 0.314M NaOH in the presence of borohydride, essentially as described in U.S. Pat. No. 3,956,273—Guiseley. The amount of derivatization actually obtained with a given amount of added chemical will depend on details of reaction scale, type of reactor, and other variables, as is known; the relative amounts shown here will provide a guide for work under other detailed conditions. Col. 5: Measured gel strength at 2% concentration of highly derivatized agarose without matrix.
 Col. 6: Functionality at 4% (total gel concentration), with up to 20wt % high gel strength (HGS) matrix material incorporated; the HGS was SeaKem Gold, unless noted (examples 20–22). These results are ratings of the performance of gels of these compositions in separating the 147 bp isomers described above. The results in columns 6 and 7 of: NO (separation) means completely outside the scope of this invention; BROAD(ening) means poor but just barely within the scope of this invention by indicating the probable presence of a doublet; YES means completely within the scope of this invention showing resolution of the doublet; and are described above more fully. Gels were run in either horizontal (3 mm thick, submarine) or vertical (1 mm thick, paired plate) formats, at about 20 V/cm of gel length, in cells of various sizes. The results were not dependent on gel format.
 Col. 7: Functionality at other conditions, abbreviated as the ratio HGS/(% total gel concentration).
Discussion of the Examples:

Examples 1–10 employed a series of agaroses of decreasing Tg. The Tg threshold at which the inventive method properties appear (Ex. 3) is fairly sharp. The widely-used prior art materials of Ex. 1 (LE, the starting material, a Gelidium agarose; and Ex. 2 (SPQ, SeaPlaque", the standard "low-melting" agarose) were not effective. The 16.5° C. highly derivatized agarose was marginally effective at high concentration, while the 14.5° C., 11° C. and 10.0° C. inventive compositions (conducted at 90 wt % highly derivatized agarose component) were quite effective. Inventive compositions gelling below 14.5° C. and above 1° C. were all effective in varying degrees. Example 9 demonstrates that 50 wt % matrix hydrocolloid diminishes but does not eliminate the desired properties of the inventive compositions. Example 11 demonstrates that the desired inventive properties can be achieved by derivatization of viscosity-reduced (i.e., partially depolymerized) agarose, if its Tg is within the inventive range. Examples 12–16 show a similar series, where the starting agarose is from naturally-methylated Gracilaria species, partially depolymerized to reduce viscosity. Example 12 is the starting material; Example 13 is the low-melting component of MetaPhor agarose, mentioned above; and 14–16 are Examples of the invention. The 15.5° C. and 14° C. materials were marginally effective; full effectiveness was seen at 7.5° C. Examples 17–19 were made by derivatizing full viscosity Gracilaria agarose; again, materials above 17° C. were not effective, and those below were effective. Examples 20–22 show the effects of varying the matrix. Gold was used in the previous examples (SeaKem" Gold agarose is of very high gel-strength, typically 1800–2000 g/cm2 at 1 wt % concentration); here other agaroses are shown to be effective as matrices without affecting the ability to obtain the inventive effect. Thus the gelling temperature (that is, degree of derivatization) of the highly derivatized component was the critical variable for achieving the inventive effect. Example 23 showed the inventive effect in an agarose derivatized with a different chemical, allyl glycidyl ether, which is commercially available as AcrylAide crosslinker (a product of FMC Corporation, BioProducts Group, Philadelphia, Pa. U.S.A.).

EXAMPLE 24

Conformational Isomer Separation (and Comparison)—FIG. 2

Figure 2A:
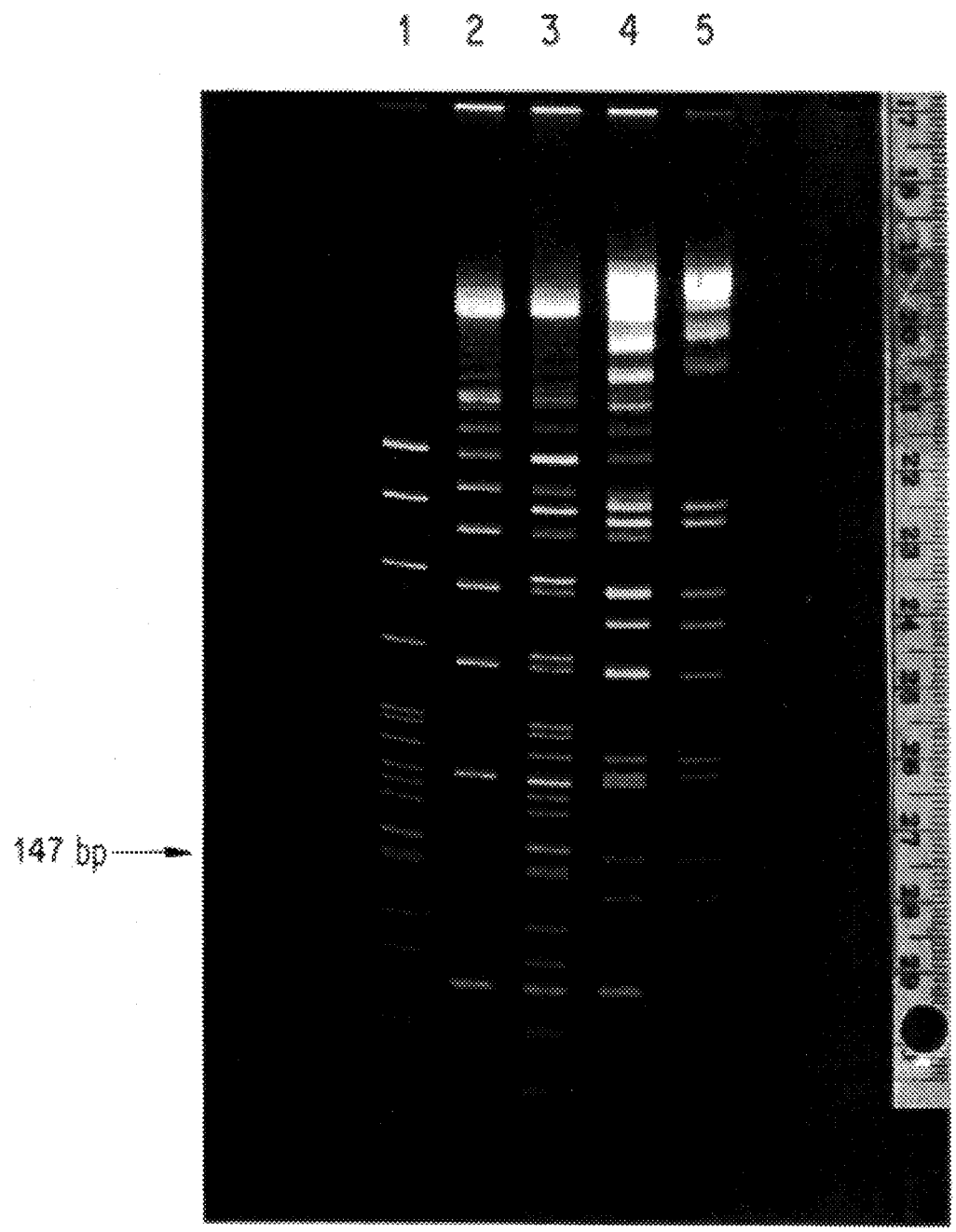
FIGS. 2A and 2B are photographs of a stained electrophoresis gel, which show an inventive conformational resolution of the 147 bp fragments on an inventive gel but not on a highly sieving prior-art gel (MetaPhor agarose).

The Msp I digest of pBR322, containing the 147 bp fragments to be separated, was separated by electrophoresis using gels comprising [1] a derivatized agarose with a Tg of 9° C. at 0.8% concentration and [2] a prior art material, Metaphor agarose, (a product of FMC Corporation, BioProducts Group, Philadelphia, Pa., U.S.A.). Photographs of the stained gels are shown in FIG. 2a (invention) and 2b (Metaphor). The two gels were made and handled identically, and had the same material in the numbered lanes. The gels were 4% agarose in 1×TBE buffer. They were cast in a vertical cell (16×26×0.1 cm) and run in a Dual Adjustable Slab Gel Unit—model DA S6-250 (from CBS Scientific Company, Inc., Del Mar, Calif., U.S.A.) at 19.2 volts/cm gel for 1.5 hours. After running, the gels were removed from the cell, stained with ethidium bromide, and photographed. Lane 1 contains 0.4 micrograms of the Msp I digest. Lane 2 is 0.6 micrograms of the "100 bp" ladder. Lane 3 contains 0.4 micrograms of the Msp I digest and 0.6 micrograms of the 100 bp ladder. Lane 4 contains 0.6 micrograms of the 100 bp ladder and the "1 kbp" ladder. Lane 5 contains the 1 kbp ladder.

Figure 2B:
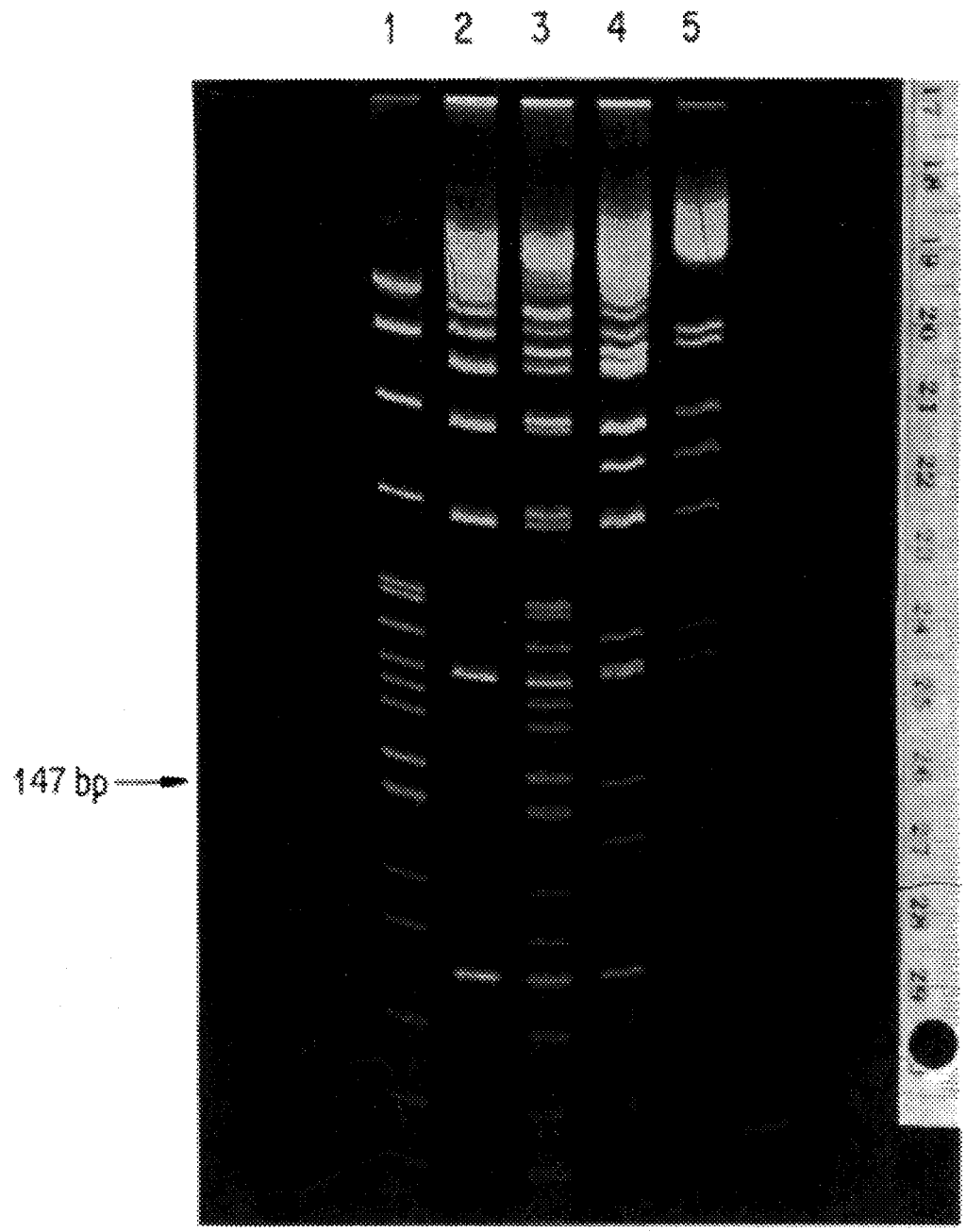

The points of interest are the 12th band from the top in lane 1, and the equivalent band in lane 3, on the two gels. In FIG. 2a (the inventive gel composition), this band is clearly split into a fine doublet. In FIG. 2b (Metaphor agarose gel), the band is not split, and not significantly broader (in the direction of migration) than other bands of like intensity. The molecular weight markers, coupled with knowledge of the sizes expected in the Msp I digest of pBR322, identifies the split band as the 147 bp band. This example demonstrates the superiority of the inventive agarose and method in separating a conformational isomer (147 bp) as compared to a comparable prior art composition.

EXAMPLE 25

Figure 3A:
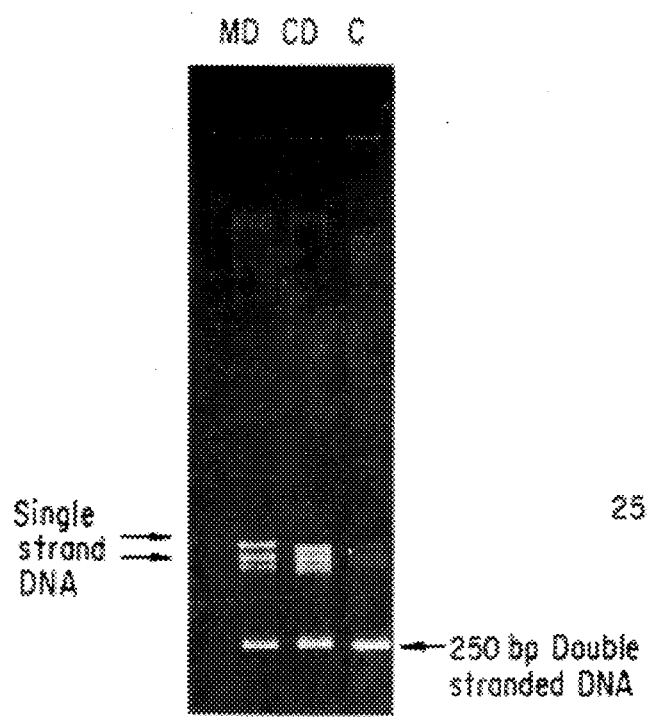
FIGS. 3A and 3B are is a photographs which show an inventive SSCP conformational separation on an inventive gel and on MetaPhor agarose.
Figure 3B:
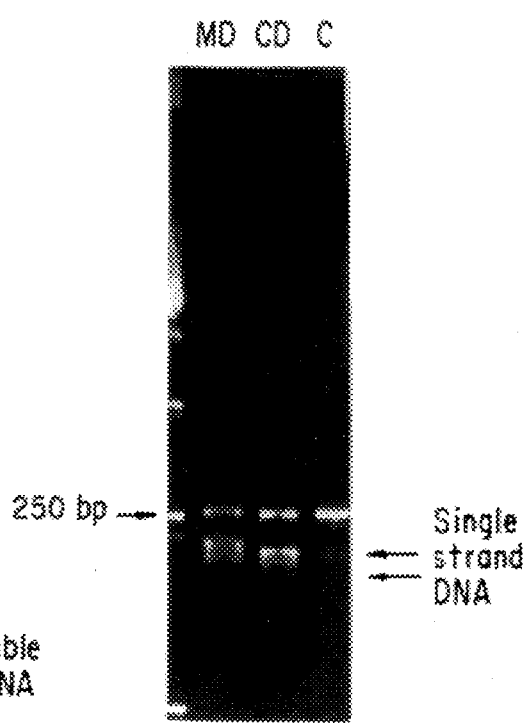

SSCP Separation land Comparison)—FIG. 3 Gels were prepared as in Example 24, containing 3% of the inventive gel composition of Example 9 (left panel), and the prior art MetaPhor agarose gel (right panel), both made in 0.5×TBE buffer. They were cast in a vertical cell (18×16×0.1 cm) and were run in a Hoefer SE600 electrophoresis chamber at 31 V/cm for one hour. The three lanes in each panel, from left to right, contain: (1) the mutant denatured DNA; (2) the wild-type (control) denatured DNA; and (3) a non-denatured wild-type control. The top 3 bright bands in the lower half of the inventive gel composition are single stranded DNA; the bright band near the bottom is control double stranded (non-denatured) DNA. The crucial diagnostic difference is the difference in migration between the mutant and wild-type single stranded DNA. These relationships are identical to that which is seen on polyacrylamide gels.

In the prior art gel (right panel), the single stranded bands are blurred together, and run faster than the double stranded control. Unlike the inventive composition gels and polyacrylamide gels the result cannot readily be used to detect single base pair changes, because the bands are not clearly resolved.

EXAMPLE 26

Separation of a heteroduplex—FIG. 4

Figures 4A, 4B:
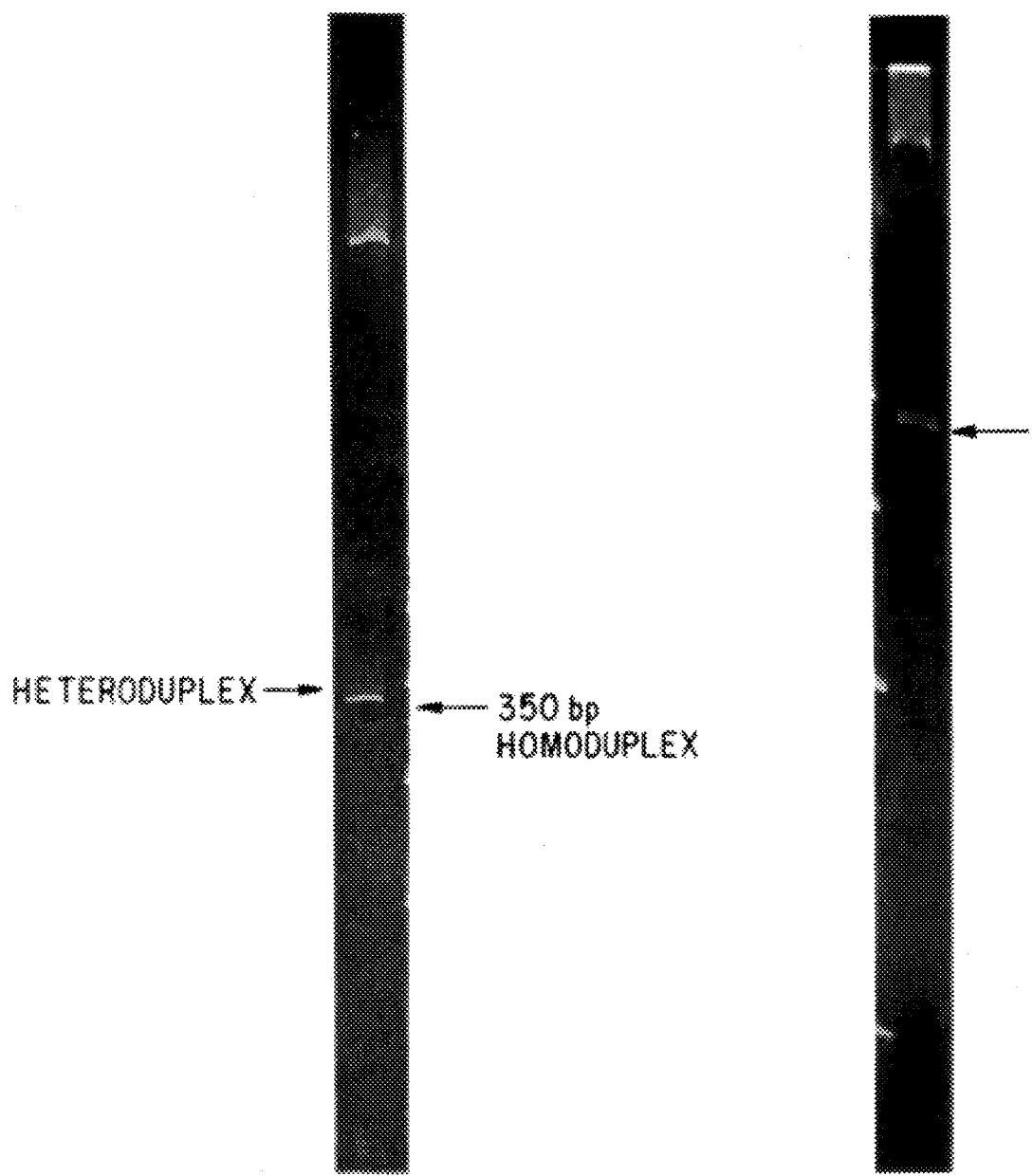
FIGS. 4A and 4B are photographs which show an inventive heteroduplex conformational separation on an inventive gel and on MetaPhor agarose.

Gels were as in Example 24, using a 4% concentration of the inventive gel of Example 9, except run for two hours. A clear separation is shown between the 350 bp heteroduplex and homoduplex on an inventive gel composition (FIG. 4A) as compared to a blurred separation on a prior art gel (FIG. 4B).

We claim:

1. A composition for the electrophoretic separation of conformational nucleic acid isomers comprising:
   A) an aqueous gel comprising
      (1) at least one agarose derivatized to the extent that it has become non-gelling or sufficiently to reduce its gelling temperature (Tg) as measured at 0.8 wt % concentration to below 9° C., present in 40 wt % or more based upon the gel total weight, in admixture with
      (2) at least one high strength agarose matrix gel present in an amount which together with the derivatized agarose gives a 100 wt % total gel weight; and
   B) an electrophoretic buffer, present in an electrophoretic buffer—effective amount.

2. A composition for the electrophoretic detection of point mutations by single strand conformational polymorphism (SSCP) analysis or heteroduplex/homoduplex analysis, or specific DNA-protein interactions by gel shift analysis comprising:
   A) an aqueous gel comprising
      (1) at least one agarose derivatized sufficiently to reduce its gelling temperature (Tg) as measured at 0.8 wt % concentration to below 9° C., present in 40 wt % or more based upon the gel total weight, in admixture with
      (2) at least one high strength agarose matrix gel present in an amount which together with the derivatized agarose gives a 100 wt % total gel weight; and
   B) an electrophoretic buffer, present in an electrophoretic buffer—effective amount.

3. The composition of claim 1 or 2 wherein the highly derivatized agarose is substituted with a: $C_{1-4}$ alkyl; hydroxy, dihydroxy or polyhydroxy-$(C_{1-5})$ alkyl; an ester or ether of the agarose with a $C_{1-4}$ neutral moiety having 0 or 1 to 3 oxygen atoms; or is a mixture of these derivatized agaroses.

4. The composition of claim 3 wherein the highly derivatized agarose is hydroxyethyl agarose.

5. The composition of claim 3 wherein the highly derivatized agarose is present in up to 90 wt %.

6. The composition of claim 3 wherein the highly derivatized agarose is present in 60 to 90 wt %.

7. The composition of claim 3 wherein the highly derivatized agarose is present in 70 to 90 wt %.

8. The composition of claim 3 wherein the highly derivatized agarose is present in about 80 wt %.

9. The composition of claim 3 wherein the derivatized agarose has a gelling temperature of from the lowest temperature at which gellation will occur to less than 9° C.

10. The composition of claim 3 wherein the derivatized agarose has a gelling temperature of 0° C. to less than 9° C.

11. The composition of claim 3 wherein the derivatized agarose has a gelling temperature of 2° C. to less than 9° C.

12. The composition of claim 3 wherein the derivatized agarose has a gelling temperature of 6° C. to less than 9° C.

13. The composition of claim 3 wherein the derivatized agarose has a gelling temperature of 6° C. to 8° C.

14. The composition of claim 11 or 12 wherein:
   A) said aqueous gel consists essentially of:
      (1) hydroxyethyl agarose having a gelling temperature of from 6° C. to less than 9° C. and present in about 70 wt % to about 90 wt %; and
      (2) a high gel-strength hydrocolloid matrix gel which is an agarose present in an amount which together with the hydroethyl agarose gives a 100 wt % total gel weight.

15. The composition of claim 1 or 2 wherein the high gel-strength agarose matrix gel has a gel strength of at least 500 g/cm at 1% w/w concentration.

16. The composition of claim 1 or 2 wherein the total gel concentration in water of the agaroses is from 2% to 10%.

17. A method for the electrophoretic separation of conformational nucleic acid isomers employing an electrophoretic composition comprising:
   A) an aqueous gel which is
      (1) at least one highly derivitized agarose derivitized to the extent that it has become non-gelling or sufficiently to reduce its gelling temperature (Tg) as measured at 0.8 wt % concentration, in water to below 17° C., present in 40 wt % or more based upon the gel total weight, in admixture with
      (2) at least one high gel-strength agarose matrix gel in an amount which together with the derivitized agarose gives a 100 wt % total gel weight; and
   B) an electrophoretic buffer, present in an electrophoretic buffer—effective amount.

18. A method for the detection of point mutations comprising Single Strand Conformational Polymorphism (SSCP) analysis by an assay using the method of claim 17.

19. A method for the detection of point mutations comprising Heteroduplex/Homoduplex analysis by an assay using the method of claim 17.

20. A method for the detection of specific DNA-protein interactions comprising Gel Shift analysis by an assay using the method of claim 17.

21. The method of claim 17, 18, 19, or 20, wherein the highly derivatized agarose is substituted with a: $C_{1-4}$ alkyl; hydroxy, dihydroxy or polyhydroxy-$(C_{1-5})$ alkyl; an ester or ether of the agarose with a $C_{1-4}$ neutral moiety having 0 or 1 to 3 oxygen atoms; or is a mixture of these derivatized agaroses.

22. The method of claim 21 wherein the highly derivatized agarose is hydroxyethyl agarose.

23. The method of claim 21 wherein the highly derivatized agarose is present in up to 90 wt %.

24. The method of claim 21 wherein the highly derivatized agarose is present in 60 to 90 wt %.

25. The method of claim 21 wherein the highly derivatized agarose is present in 70 to 90 wt %.

26. The method of claim 21 wherein the highly derivatized agarose is present in about 80 wt %.

27. The method of claim 5 wherein the derivatized agarose has a gelling temperature below 17° C.

28. The method of claim 21 wherein the derivatized agarose has a gelling temperature of 0° C. to less than 17° C.

29. The method of claim 21 wherein the derivatized agarose has a gelling temperature of 2° C. to less than 17° C.

30. The method of claim 21 wherein the derivatized agarose has a gelling temperature of 6° C. to less than 9° C.

31. The method of claim 23 wherein the derivatized agarose has a gelling temperature of 6° C. to 8° C.

32. The method of claim 1 wherein the high gel-strength agarose matrix gel has a gel strength of at least 500 g/cm at 1% w/w concentration.

33. The method of claim 1 wherein the total gel concentration in water of the agaroses is from 2% to 10%.

* * * * *